United States Patent [19]
Zoltan et al.

[11] Patent Number: 4,926,852
[45] Date of Patent: May 22, 1990

[54] MEDICATION DELIVERY SYSTEM PHASE ONE

[75] Inventors: Bart J. Zoltan, Old Tappan, N.J.; Beth L. Laube; George K. Adams, III, both of Baltimore, Md.

[73] Assignee: The Johns Hopkins University, Baltimore, Md.

[21] Appl. No.: 251,454

[22] Filed: Sep. 30, 1988

Related U.S. Application Data

[63] Continuation-in-part of Ser. No. 877,331, Jun. 23, 1986, Pat. No. 4,790,305.

[51] Int. Cl.$^5$ .............................................. A61M 11/00
[52] U.S. Cl. ........................... 128/200.23; 128/203.24
[58] Field of Search ............. 128/200.4, 200.2, 200.23, 128/205.11, 200.18, 203.12, 203.24, 205.13, 205.17, 205.21, 205.24, 205.25; 272/203.15, 99

[56] References Cited

U.S. PATENT DOCUMENTS

| | | | |
|---|---|---|---|
| 2,788,784 | 4/1957 | Birch et al. | 128/200.23 |
| 2,944,546 | 7/1960 | Ziherl et al. | 128/205.17 |
| 4,484,577 | 11/1984 | Sackner et al. | 128/200.23 |
| 4,534,343 | 8/1988 | Nowacki et al. | 128/200.23 |
| 4,612,926 | 9/1988 | Boiarski et al. | 128/200.21 |
| 4,796,614 | 1/1989 | Nowacki et al. | 128/200.25 |
| 4,919,097 | 10/1978 | Spector | 128/205.25 |

FOREIGN PATENT DOCUMENTS

| | | | |
|---|---|---|---|
| 933216 | 4/1948 | France | 128/200.28 |
| 2110543 | 6/1983 | United Kingdom | 128/200.23 |

*Primary Examiner*—Max Hindenburg
*Assistant Examiner*—K. M. Reichle
*Attorney, Agent, or Firm*—Cushman, Darby & Cushman

[57] ABSTRACT

An apparatus for use in inhaling pharmaceutical aerosols. The apparatus includes a mouthpiece and a rigid housing for receiving an aerosolized medicine. The rigid housing has one or more orifices which are spaced from the mouth piece so that flow through the housing is possible but is limited by the orifice(s) to a desired volumetric flow rate. The patient is aided by having the initial velocity of the aerosolized medicine reduced to zero by virtue of the initial delivery of the same to the housing interior, and by having the volumetric flow rate of the inhaled medication maintained below required limits thereby providing the conditions for optimal dosing. Further, the ability of the patient to inhale to total lung capacity with the flow through chamber enhances penetration of aerosolized drug to the lung periphery, and improves the ease of use for the patient.

8 Claims, 5 Drawing Sheets

MEDICATION DELIVERY SYSTEM PHASE ONE

This is a continuation-in-part of Ser. No. 06/877,331 filed June 23, 1986, now U.S. Pat. No. 4,790,305.

BACKGROUND OF THE INVENTION

Field of The Invention

This invention relates to the dispensing of pharmaceuticals which are active when administered as aerosols and, more specifically, to the dispensing of aerosol pharmaceuticals for the treatment of pulmonary diseases.

Certain medications, especially those intended for the treatment of acute and chronic respiratory disorders, for example, bronchodilators which are used in the treatment of bronchospasm and mucosal edema, are most effective when inhaled directly into the lungs. Similarly, antibiotic aerosols used to treat bronchial infections, antiinflammatory steroids used for the treatment of asthma, antifoaming agents for the treatment of fulminant pulmonary edema, and cromolyn sodium for controlling allergic asthma are most effective when administered in this manner. Thus, numerous pharmaceutical products are marketed as aerosols administered from metered dose inhalers.

While aerosol therapies have been very successful, there have been a number of difficulties in dispensing the aerosols properly.

A major problem of aerosol therapy is achieving deposition of the aerosol on the walls of small bronchi and brochioles, where the action of the medication is most often required. Less than ten percent of the medication delivered by standard metered dose inhalers reaches the typical patient's lungs. Most of the ninety percent of the medication which does not penetrate to the target area is deposited in the mouth, throat, and trachea, and is eventually ingested. A small fraction of the aerosol is exhaled. The medication which deposits in the mouth and throat may lead to dysphonia and/or oral and laryngeal candidiasis while the medication which is ingested serves no medical purpose to the patient and is responsible only for undesirable side effects.

Therefore the delivery of some drugs via aerosol has been considered impractical. Nevertheless the aerosol delivery of many drugs, if possible, would present an attractive alternative to the therapies that are currently available. An example of such a substance is polypeptides.

Polypeptides are made up of amino acid sequences, and include large molecules like insulin, and all of the products of recombinant DNA (rDNA) techniques. These molecules are broken down in the digestive tract and, therefore, the intact polypeptide molecule is not absorbed into the bloodstream. Accordingly, the only practical way to administer these drugs is by injection, although the nasal route of administration would be desirable and has been suggested, but has not been practical.

Another example is tissue plasminogen activator (t-PA) which appears to be successful in halting damage done to cardiac muscle during myocardial infarction. There could be an advantage to being able to utilize this drug as an aerosol for inhalation so that it could be administered without the need to wait for a physician or paramedic.

Delivery of therapy in pneumonia directly to the lung would also be desirable. Ordinarily, the concentration of antibiotic in the sputum is only two to three percent of the concentration in blood. However, in pneumonia, antibiotic concentration in the sputum is believed to be the determining factor for efficacy of the therapy. Therefore, direct delivery of the antibiotic may improve the effectiveness of the treatment.

In order to avoid the problems encountered with aerosol delivery, noted above, the aerosol should consist of small particles, less than 5 microns, since larger particles cannot negotiate the sharp turns to the lung and are deposited in the oropharynx due to inertial effects. Particles that persist in the airstream beyond the oropharynx may deposit in the larynx and on the walls of the trachea and large bronchi as a result of turbulence, particularly if the patient inhales at a volumetric flow rate above 30 liters per minute.

Metered dose inhalers deliver aerosol at a very high velocity directly into the patient's mouth, and most of the medication impacts and is deposited in the mouth. This high initial velocity of the aerosol is a major factor in the ineffectiveness of many inhaler systems. In order to minimize mouth deposition it has been determined that the volumetric flow rate of the inhaled aerosol should be below 30 liters per minute.

After the medication has been inhaled it is best to continue inhaling to total lung capacity to promote greater penetration of drug to the lung periphery. One should then hold that breath for four to ten seconds, if possible, to allow for sedimentation of particles onto the airway surface.

Several pharmaceutical manufacturers have included, or sold separately with their aerosol products, what they refer to variously as "spacers", "inhalers", "drug inhalers", "oral adapters", "spacer-inhalers", and "spray inhalers" to be used in conjunction with their products.

Of the related devices known to the inventors, only Sackner et al., U.S. Pat. No. 4,484,577, marketed as the InspirEase from Key Pharmaceutical, addresses the known problems of aerosol inhalation. The InspirEase is essentially a collapsible bag into which the medication is metered, and from which the patient inhales. The InspirEase mouthpiece contains a whistle which is silent at low flow rates but sounds when the patient is inhaling too rapidly.

Further, laboratory equipment has been developed which allows inspired air to be measured using a pneumotachograph. The flow rate signal is integrated by a computer, and an aerosol canister containing the medication is actuated automatically at a predetermined lung volume using a solenoid mounted on top of the aerosol actuator. While this system is suitable for experimental studies, it is impractical for use in routine therapy because of size and cost.

Thus, there is a need for a device to aid patients in taking their aerosol medications. The device should limit the volumetric flow rate of the medication aerosol as it enters the mouth, and it should allow the patient to inhale to total lung capacity. The size of the device should allow it to be carried by the patient without too much inconvenience, and the cost to the patient should be low.

SUMMARY OF THE INVENTION

Briefly, the apparatus described in Ser. No. 877,331 now U.S. Pat. No. 4,790,305 delivered a volume of unmedicated air from a collapsible holding chamber to the patient, after which it automatically began to deliver the aerosolized medication. The volumetric flow rate of the inhaled medication was maintained below the upper limits of volumetric flow rate for optimal dosing. While that design met all of the criteria for a safe and effective design, the method of holding a volume of unmedicated air can be very cumbersome.

In addition, there is lack of agreement as to the precise optimum in lung volume at the time of inhalation that will maximize the benefit from inhaled aerosols. In the medical literature, the optimal lung volume that is recommended ranges from 20 percent to 80 percent of vital capacity.

The apparatus described in this co-pending application eliminates the cumbersome volume of unmedicated air altogether, while it overcomes some of the disadvantages associated with prior attempts, and provides the patient and his physician with a practical means of taking aerosol medication in an optimal manner at low cost. This is achieved by metering the aerosol medication into a rigid chamber, from which the patient inhales the medication. The chamber is of a flow-through design, so that the patient may continue to inhale from the chamber even after the initial volume has been inspired. Throughout this specification, the term rigid chamber refers to the chamber while in use. Indeed, for the sake of portability, it is desirable to fold or collapse the subject invention into a small space. Thus the term rigid is meant to be applied in the same way that an umbrella may be described as rigid when in use, although it can be stored in a closed configuration and extended prior to use.

The volumetric flow rate is limited by the use of orifices at the back of the chamber. The orifices are nominally sized for the typical frail patient, with provisions for closing one or several orifices if the physician or the patient feels that the nominal setting is inappropriate for a specific patient.

In use, the aerosol medication is metered into the rigid chamber. The patient inhales through a single mouthpiece. As the patient begins to inhale from the rigid chamber containing the medication, his volumetric flow rate is limited to 30 liters per minute by the orifices described above. The patient continues to inhale until he reaches his total lung capacity, at which time he holds his breath for the time recommended by his physician.

Other objects, features and characteristics of the present invention, as well as the methods of operation and functions of the related elements of the structure, and the combination of parts and economies of manufacture, will become more apparent upon consideration of the following detailed description and the appended claims with reference to the accompanying drawings all of which form a part of this specification, wherein like reference numerals designate corresponding parts in the various figures.

BRIEF DESCRIPTION OF THE DRAWINGS

FIG. 1A is a perspective view of the mouthpiece of the invention;

FIG. 1B is a cross-sectional view of the mouthpiece of the present invention;

FIG. 2A is a view of the rigid chamber of the invention;

FIG. 2B is a cross-sectional view of the rigid chamber of the invention;

FIG. 2C is a detailed elevational view of the apertures in the end piece of the rigid chamber;

FIG. 3 is a perspective view of the assembled device;

FIG. 4A is a cross-sectional view of the drawing of an alternate embodiment of the invention, wherein the source of the aerosol, and the mouthpiece are not integral to the invention;

FIG. 4B is an elevational view of the end of the chamber of FIG. 4A;

FIG. 5A is an elevational view of an alternate embodiment of the invention, wherein the device is collapsible;

FIG. 5B shows the device of FIG. 5A in its collapsed configuration;

FIG. 6A is an image of the oropharyngeal deposition of radiolabelled inhalant inhaled using a prior-art device, a DeVilbiss nebulizer;

FIG. 6B is an image of the bronchopulmonary deposition of radiolabelled inhalant inhaled using a prior-art device, a DeVilbiss nebulizer;

FIG. 6C is an image of the oropharyngeal deposition of radiolabelled inhalant inhaled using a DeVilbiss nebulizer in conjunction with the subject invention; and FIG. 6D is an image of the bronchopulmonary deposition of radiolabelled inhalant inhaled using a DeVilbiss nebulizer in conjunction with the subject invention.

DETAILED DESCRIPTION OF THE PRESENTLY PREFERRED EXEMPLARY EMBODIMENTS

The mouthpiece 10 of the invention is shown in FIGS. 1A and 1B. The proximal end 12 of the mouthpiece 10 is shaped to be accommodated in the mouth of the patient. In the preferred embodiment, a standard aerosol medication is administered from a metered dose inhaler 14 which is mounted to a coupling 16, which is designed to accommodate metered dose inhalers. Passage 18 directs the aerosol from the metered dose inhaler 14 out through the distal end of the mouthpiece. The distal end of the mouthpiece also has keys **20*a* and 20*b*, for example, which allow the mouthpiece 10 to be attached to the rigid chamber 30**.

As shown in FIG. 2A, rigid chamber 30, has cut outs 32, which allow chamber 30 to be rigidly attached via keys 20A and 20B to the mouthpiece 10. An aperture 34 allows the contents of metered dose inhaler 14 to be directed into chamber 30. Endwall 33 of chamber 30 opposite end 31 has a plurality of small orifices **36*a–i*** defined therethrough as can be seen in FIGS. 2B and 2C. In the preferred embodiment nine orifices, each about 0.020 inches in diameter are used. Depending on the age and health of the patient, orifices can be covered in any suitable manner, one at a time, until the volumetric flow rate for the patient is below 30 liters per minute. The covered orifices may be permanently sealed.

FIG. 3 is a perspective view of the preferred embodiment, assembled, and ready for use.

The invention was evaluated in a normal subject at the Johns Hopkins University Hospital. The results of this evaluation are reported below.

The normal subject was studied at the same time of day on two study days. On the first study day, the subject inhaled a 0.9% saline solution containing the radioisotope Tc-99m sulfur colloid ad libitum using a prior art device, a DeVilbiss #42 nebulizer. This nebulizer was connected to a 20 p.s.i. compressed air source through a nebulization dosimeter (Laboratory for Applied Immunology—Baltimore, Md.), which controlled the duration of the compressed air pulse during aerosol generation. A manual trigger, controlled by the subject, was used to actuate the nebulizer air flow for a period of 0.6 seconds.

Figure 1A:
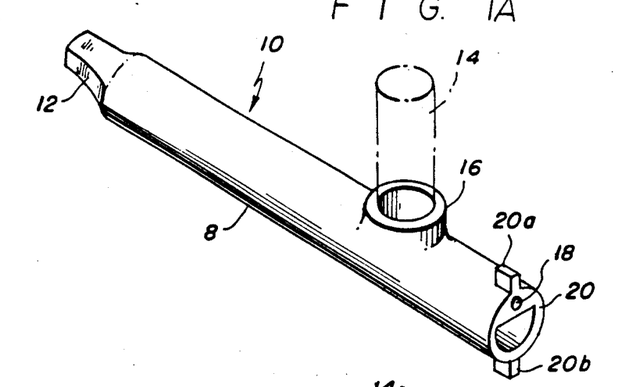
Figure 1B:
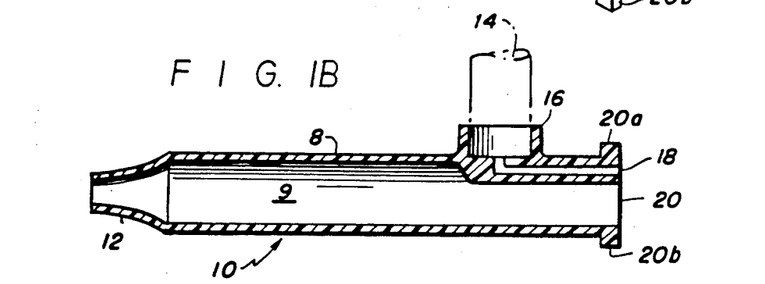
Figure 2:
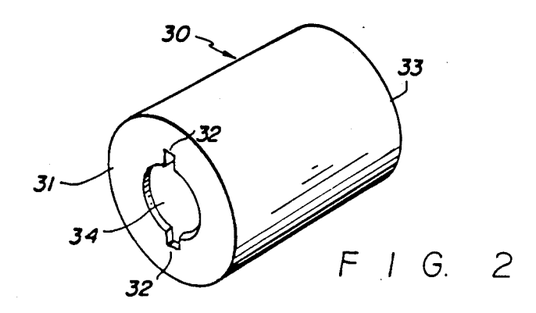
Figure 2B:
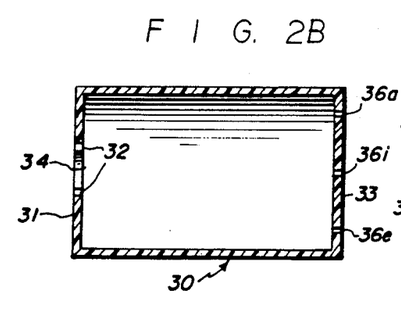
Figure 2C:
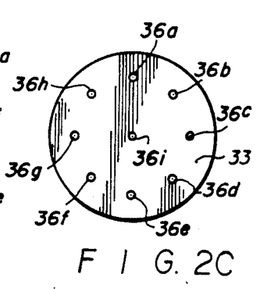
Figure 3:
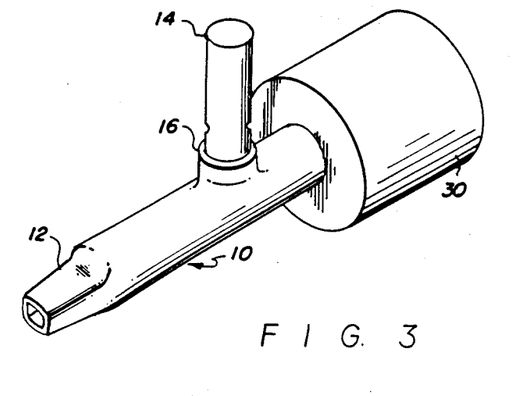
Figure 4A:
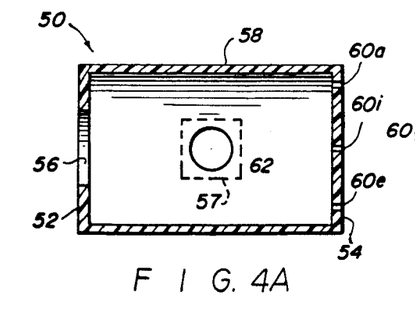
Figure 4B:
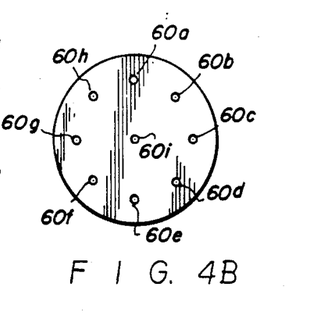
Figure 5A:
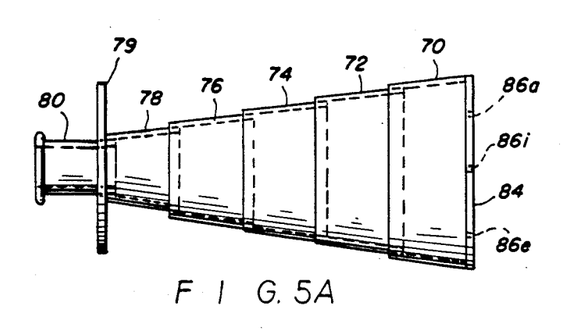
Figure 5B:
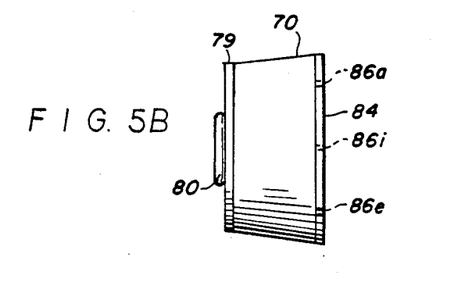
Figure 6A:
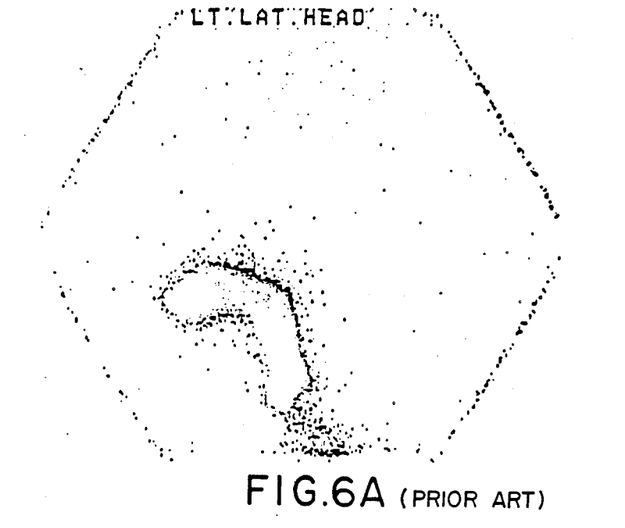
Figure 6B:
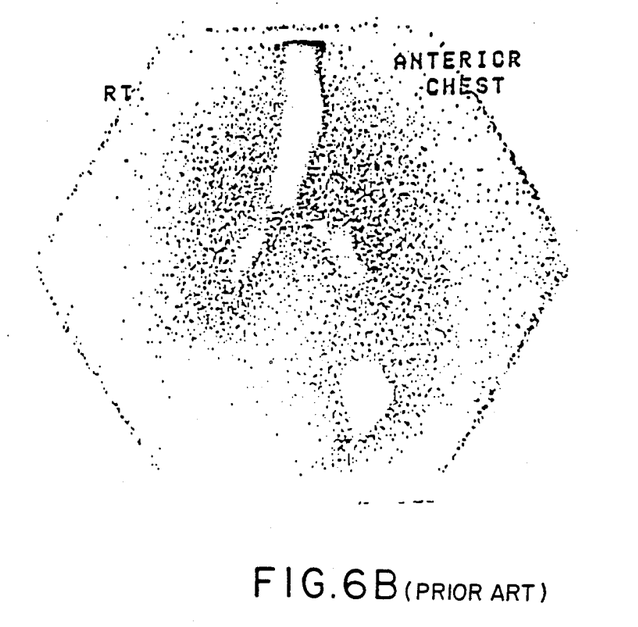
Figure 6C:
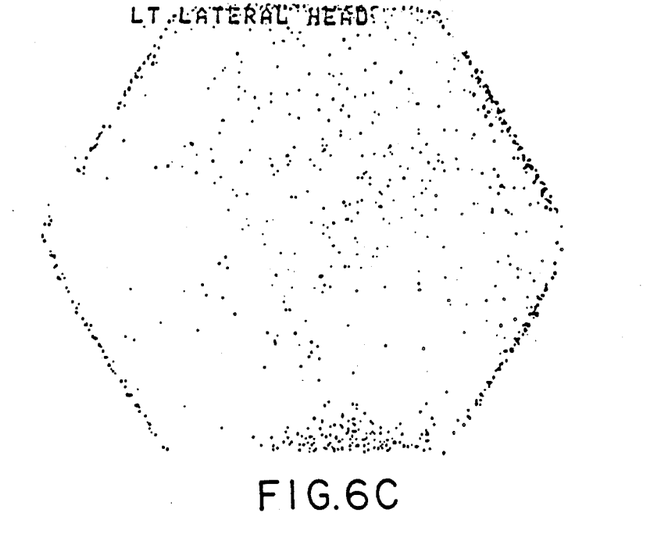
Figure 6D:
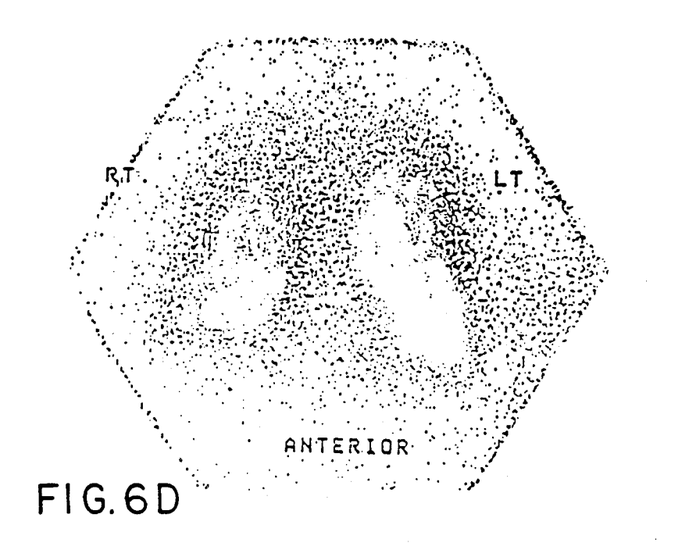

On the second study day, the subject inhaled the same radioaerosol using the #42 DeVilbiss nebulizer in conjunction with the present invention. Actuation of the nebulizer airflow was manually triggered, at which time radioaerosol was delivered to the rigid chamber of the subject invention. The subject inhaled the radioaerosol from the rigid chamber to total lung capacity, at which time the subject exhaled slowly with no breath holding.

Following the inhalation of the radioaerosol, the subject's left lateral skull and lungs were scanned for ten minutes each with a Technicare Model #110 gamma camera. Counts from the gamma camera were acquired in a 256 by 256 picture element (pixel) matrix and were processed for oropharyngeal and bronchopulmonary deposition in a 64 by 64 pixel matrix using an Informatek SIMIS 2 computer. Aerosol deposited in the oropharynx and the bronchopulmonary region was expressed as a percent of total counts in the two regions.

Intrapulmonary aerosol deposition was further quantified in terms of aerosol initially deposited within an inner, intermediate, and outer zone of the right lung (anterior image). These zones are circular crescents dividing the radius of the right lung to its outer boundary into three equal segments. The left anterior lung image was not used for this analysis because its inner and intermediate zone activities are attenuated by the heart. Counts within each of the three lung zones were divided by the number of picture elements (pixels) in each zone, mean counts/pixel, and the mean counts/pixel in each zone were compared. For this analysis it was assumed that the inner zone is comprised predominantly of large central airways, while the outer zone reflects terminal airways and alveoli. The intermediate zone includes a combination of large and small airways as well as alveolar regions of the lung. An inner-to-outer ratio of counts per pixel of 1.00 would indicate a homogenous distribution of the aerosol within the lungs. The scan images were photographed directly from the computer display using a 35 mm camera. Scan photos were reproduced for display as glossy prints on high contrast film.

FIGS. 6A and 6B are gamma camera images of the left lateral skull, and of the anterior chest following inhalation of the radiolabelled aerosol by one normal subject using a prior-art device, a DeVilbiss #42 nebulizer. Oropharyngeal deposition was 63 percent of total counts and bronchopulmonary deposition was 37 percent of total counts.

FIGS. 6C and 6D are gamma camera images, in the same subject, of the left lateral skull and of the anterior chest following inhalation of the radiolabelled aerosol using the same nebulizer in conjunction with the subject invention. Oropharyngeal deposition was 3 percent of total counts and bronchopulmonary deposition was 97 percent of total counts.

Table 1 shows the regional analysis of the anterior lung images of radiolabelled aerosol deposition using the DeVilbiss #42 nebulizer, and the DeVilbiss #42 nebulizer together with the subject invention. A reduction in the Inner:Outer zone ratio following administration of the radioaerosol using the DeVilbiss #42 nebulizer with the subject invention indicates an increase in distribution homogeneity within the lungs.

TABLE 1

REGIONAL DEPOSITION OF RADIOLABELLED AEROSOL

| | DeVilbiss #42 nebulizer | DeVilbiss #42 nebulizer with the subject invention |
|---|---|---|
| Right inner lung: | | |
| Counts | 3,158 | 2,570 |
| No. of pixels | 75 | 75 |
| Counts per pixel | 42.11 | 34.27 |
| Right middle lung: | | |
| Counts | 4,682 | 7,254 |
| No. of pixels | 201 | 201 |
| Counts per pixel | 23.29 | 36.09 |
| Right outer lung: | | |
| Counts | 2,284 | 6,274 |
| No. of pixels | 247 | 247 |
| Counts per pixel | 9.25 | 25.29 |
| Ratio of counts per pixel: | | |
| Inner:/Outer | 4.35 | 1.36 |
| Inner:/Middle | 1.81 | 0.95 |
| Middle:/Outer | 2.52 | 1.43 |

Table 2 shows the statistical distribution of the deposition of the radiolabelled aerosol using the Devilbiss #42 nebulizer, and the DeVilbiss #42 nebulizer together with the subject invention. A reduction in values of skew (a measure of distribution asymmetry) and Kurtosis (a measure of distribution range) following administration of the radioaerosol with the DeVilbiss #42 nebulizer in conjunction with the subject invention indicates an increase in aerosol distribution homogeneity within the lungs.

TABLE 2

STATISTICS OF THE RADIOLABELLED IMAGES

| | DeVilbiss #42 nebulizer | DeVilbiss #42 Nebulizer with the subject invention |
|---|---|---|
| Mean counts per picture element | 10.60 | 21.18 |
| Standard deviation | 8.79 | 12.88 |
| Skew | 2.64 | 0.43 |
| Kurtosis | 10.21 | 1.74 |

FIGS. 4A and 4B show an alternate embodiment of the invention. A rigid chamber 50, is provided having a proximal end 52, and a distal end 54, and a main body 58 therebetween. The proximal end 52 has an aperture 56, which is sized to accept standard disposable mouthpieces currently in use with hospital nebulizers. The body of the device 58 also has an opening 62 of a size suitable for coupling to an external source of aerosolized medication thereto. A means for closing the opening is further provided in accordance with the present invention. If the external source of aerosolized medication is retained in the opening, then that container will close the opening. In the alternative, the opening can be closed after delivery of medicament to the chamber. The means for closing is shown schematically by phantom box 57 and may be any conventional means for closing such as, for example, a piece of tape or a one-way valve structure. The distal end of the device 54, having a multiplicity of flow restricting orifices 60*a–i* (FIG. 4B).

Another alternate embodiment of the invention is shown in FIGS. 5A and 5B. The rigid chamber in this embodiment is collapsible, thereby making the invention more portable, and less noticeable when carried. Many patients, especially pediatric patients are embarrassed by their need to take medication, and this embodiment minimizes size and obtrusiveness. In FIG. 5A, the device is shown in its extended form, ready for use. The largest component piece, a truncated cone segment 70, has rate limiting orifices shown as 86a–c. Other similar offices are provided but not shown in particular. Truncated cone segments 70–78, nest inside one another and are thereby collapsible. Segment 78 also has a circular flange 79, the diameter of which is at least the size of the small diameter of the largest piece 70. With this arrangement the pieces cannot inadvertently fall apart. A mouthpiece 80 is provided with a flared end sized to fit inside piece 78, and with an opening of sufficient diameter to allow a patient to inhale therethrough in an unrestricted manner.

While the invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

We claim:

1. An apparatus for delivering medication to a patient, comprising:

a mouthpiece, said mouthpiece having a proximal end, a distal end, and means for coupling a medication container thereto intermediate said proximal and distal ends, said proximal end being shaped to be accommodated by a human mouth, said mouthpiece having first and second passages defined therethrough, said first passage extending from said proximal end to said distal end and said second passage extending from said means for coupling to said distal end; and a rigid housing, said rigid housing having a first end, a second end, and a main body portion so as to define a chamber therewithin, said first end having an aperture defined therethrough, said housing being coupled to said mouthpiece so that said chamber is fluidly coupled to said first and second passages at said distal end of said mouthpiece through said aperture in said first end, said rigid housing further having at least one orifice defined through at least one of said first end, said second end, and said main body portion for limiting the volumetric flow rate of air into said chamber;

whereby, medication can be delivered through said second passage into said chamber and, by breathing in through said first passage from said proximal end of said mouthpiece, a patient can inhale medicated air from the chamber and then continue inhaling to his total lung capacity.

2. The apparatus according to claim 1, wherein said means for coupling comprises means for coupling a medication container containing a pressurized aerosol.

3. The apparatus according to claim 1, wherein said means for coupling comprises means for coupling a medication container having a spray dispenser.

4. The apparatus according to claim 1, wherein said at least one orifice limits the volumetric flow of air into said rigid housing to 30 liters per minute or less under the influence of normal inhalation force.

5. The apparatus according to claim 4, wherein there are at least two orifices and at least one of said orifices may be closed off.

6. The invention according to claim 1, wherein said main body portion of said rigid housing is defined by axially collapsible wall means.

7. The invention according to claim 6, wherein said axially collapsible wall means comprises a plurality of rigid wall elements coupled together in side-by-side relation, said wall elements each having a different cross-section and being coupled together in order of increasing cross-section, and so as to be slidably receivable within a next adjacent, larger wall element.

8. An apparatus for aiding a patient in inhaling medication, comprising:

a mouthpiece, said mouthpiece having a proximal end, a distal end, and means for coupling a medication container thereto intermediate said proximal and distal ends, said proximal end being shaped to be accommodated by a human mouth, said mouthpiece having first and second passages defined therethrough, said first passage extending from said proximal end to said distal end and said second passage extending from said means for coupling to said distal end;

a first rigid housing, said rigid housing having a first end, a second end, and a main body portion so as to define a chamber therewithin, said first end having an opening defined therethrough, said first rigid housing being coupled to said mouthpiece so that said chamber is fluidly coupled to said first and second passages at said distal end of said mouthpiece through said opening in said first end, said rigid housing further having at least one orifice defined through at least one of said first end, said second end, and said main body portion for limiting the volumetric flow rate of air into said chamber; and means for closing off said at least one orifice until the volumetric flow rate through said orifices is at or below 30 liters per minute;

whereby medication can be delivered into said chamber through said second passage and a patient can inhale air containing the medication from the chamber through the first passage of the mouthpiece.

* * * * *

REEXAMINATION CERTIFICATE (2584th)
United States Patent [19]

Zoltan et al.

[11] B1 4,926,852

[45] Certificate Issued  May 23, 1995

[54] MEDICATION DELIVERY SYSTEM PHASE ONE

[75] Inventors: Bart J. Zoltan, Old Tappan, N.J.; Beth L. Laube; George K. Adams, III, both of Baltimore, Md.

[73] Assignee: The Johns Hopkins University, Baltimore, Md.

Reexamination Request:
No. 90/003,207, Sep. 30, 1993

Reexamination Certificate for:
Patent No.: 4,926,852
Issued: May 22, 1990
Appl. No.: 251,454
Filed: Sep. 30, 1988

Related U.S. Application Data

[63] Continuation-in-part of Ser. No. 877,331, Jun. 23, 1986, U.S. Pat. No. 4,790,305.

[51] Int. Cl.$^6$ .............................................. A61M 11/00
[52] U.S. Cl. ............................ 128/200.23; 128/203.24
[58] Field of Search ...................... 128/206.14–200.23, 128/203.15, 205.11, 203.12, 203.24, 205.13, 205.17, 205.21, 205.24, 205.25, 200.24; 272/99

[56] References Cited

U.S. PATENT DOCUMENTS

| | | | |
|---|---|---|---|
| 2,501,279 | 3/1950 | Kark | 128/266 |
| 2,709,577 | 5/1955 | Pohndorf et al. | 261/2 |
| 2,865,370 | 12/1958 | Gattone | 128/173 |
| 3,045,671 | 7/1962 | Updegraff | 128/203 |
| 3,236,458 | 2/1966 | Ramis | 239/338 |
| 3,264,683 | 8/1966 | Lloyd | 18/2.4 |
| 3,522,806 | 8/1970 | Szekely | 128/173 |
| 3,592,357 | 7/1971 | Welch | 222/193 |
| 3,681,500 | 8/1972 | Zeile et al. | 514/304 |
| 3,744,681 | 7/1973 | Morane | 222/402.12 |
| 3,789,843 | 2/1974 | Armstrong et al. | 128/200.23 |
| 3,809,084 | 5/1974 | Hansen | 128/266 |
| 3,809,294 | 5/1974 | Torgeson | 222/182 |
| 3,838,686 | 10/1974 | Szekely | 128/173 |
| 3,864,326 | 2/1975 | Babington | 261/142 |
| 3,897,779 | 8/1975 | Hansen | 128/266 |
| 3,994,421 | 11/1976 | Hansen | 222/182 |
| 4,150,071 | 4/1979 | Pecina | 261/78 |
| 4,228,795 | 10/1980 | Babington | 128/200.22 |
| 4,292,966 | 10/1981 | Monöet al. | 128/200.23 |
| 4,470,412 | 9/1984 | Nowacki et al. | 128/200.18 |
| 4,592,348 | 6/1986 | Waters, IV et al. | 128/200.23 |
| 4,706,663 | 11/1987 | Makiej | 128/200.18 |
| 4,790,305 | 12/1988 | Zoltan et al. | . |
| 4,796,614 | 1/1989 | Nowacki et al. | 128/200.14 |
| 4,852,561 | 8/1989 | Sperry | 128/200.23 |
| 4,940,051 | 7/1990 | Lankinen | 128/200.18 |
| 5,042,467 | 8/1991 | Foley | 128/200.23 |
| 5,320,044 | 6/1994 | Laube et al. | . |

FOREIGN PATENT DOCUMENTS

| | | | |
|---|---|---|---|
| 452438 | 11/1948 | Canada . | |
| 0009667 | 4/1980 | European Pat. Off. | 128/200.23 |
| 9667 | 4/1980 | European Pat. Off. | A61M 15/00 |
| 0045419 | 10/1982 | European Pat. Off. | A61M 15/00 |
| 28363 | 2/1925 | France . | |
| 296194 | 5/1916 | Germany . | |
| 1046264 | 12/1956 | Germany . | |
| 134730 | 8/1976 | Norway | A61M 15/00 |
| 7103839 | 2/1976 | Sweden | A61M 11/00 |
| 415957 | 11/1980 | Sweden . | |
| 65826 | 9/1913 | Switzerland . | |
| 623955 | 5/1948 | United Kingdom | 69/11 |
| 958867 | 5/1964 | United Kingdom . | |
| 975754 | 11/1964 | United Kingdom . | |
| 2110543 | 6/1983 | United Kingdom | 128/200.23 |
| 8502778 | 7/1985 | WIPO . | |

*Primary Examiner*—Randall Green

[57] ABSTRACT

An apparatus for use in inhaling pharmaceutical aerosols. The apparatus includes a mouthpiece and a rigid housing for receiving an aerosolized medicine. The rigid housing has one or more orifices which are spaced from the mouth piece so that flow through the housing is possible but is limited by the orifice(s) to a desired volumetric flow rate. The patient is aided by having the initial velocity of the aerosolized medicine reduced to zero by virtue of the initial delivery of the same to the housing interior, and by having the volumetric flow rate of the inhaled medication maintained below required limits thereby providing the conditions for optical dosing. Further, the ability of the patient to inhale to total lung capacity with the flow through chamber enhances penetration of aerosolized drug to the lung periphery, and improves the ease of use of the patient.

REEXAMINATION CERTIFICATE ISSUED UNDER 35 U.S.C. 307

TEH PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-5 and 8 is confirmed.

Claims 6-7 are cancelled.

New claim 9 is added and determined to be patentable.

9. *An apparatus for delivering medication to a patient, comprising:*

*a mouthpiece, said mouthpiece having a proximal end, a distal end, and means for coupling a medication container thereto intermediate said proximal and distal ends, said proximal end being shaped to be accommodated by a human mouth, said mouthpiece having first and second passages defined therethrough, said first passage extending from said proximal end to said distal end and said second passage extending from said means for coupling to said distal end; and*

*a rigid housing, said rigid housing having a first end, a second end, and a main body portion so as to define a chamber therewithin, said first end having an aperture defined therethrough, said housing being coupled to said mouthpiece so that said chamber is fluidly coupled to said first and second passages at said distal end of said mouthpiece through said aperture in said first end, said rigid housing further having at least two orifices defined through at least one of said first end, said second end, and said main body portion for limiting the volumetric flow rate of air into said chamber; whereby medication can be delivered throgh said second passage into said chamber and, by breathing in through said first passage from said proximal end of said mouthpiece, a patient can inhale medicated air from the chamber and then continue inhaling to his total lung capacity.*

* * * * *